United States Patent
Duggal et al.

(10) Patent No.: US 9,414,865 B2
(45) Date of Patent: Aug. 16, 2016

(54) JOINT AND BONE FIXATION

(75) Inventors: Neil Duggal, London (CA); Dylan Hushka, Gilbert, AZ (US); Nicholas Slater, Chandler, AZ (US); Joshua Butters, Chandler, AZ (US)

(73) Assignee: Synergy Disc Replacement INC., Kitchener (CA)

( * ) Notice: Subject to any disclaimer, the term of this patent is extended or adjusted under 35 U.S.C. 154(b) by 0 days.

(21) Appl. No.: 13/367,308

(22) Filed: Feb. 6, 2012

(65) Prior Publication Data

US 2013/0110183 A1 May 2, 2013

Related U.S. Application Data

(60) Provisional application No. 61/554,218, filed on Nov. 1, 2011.

(51) Int. Cl.
*A61B 17/70* (2006.01)
*A61B 17/80* (2006.01)
*A61B 17/16* (2006.01)
*A61B 17/86* (2006.01)

(52) U.S. Cl.
CPC ........... *A61B 17/7064* (2013.01); *A61B 17/808* (2013.01); *A61B 17/809* (2013.01); *A61B 17/1671* (2013.01); *A61B 17/864* (2013.01)

(58) Field of Classification Search
CPC ............. A61B 17/683; A61B 17/7064; A61B 17/7068
USPC ............ 606/54, 300, 324, 328–330, 247–279
See application file for complete search history.

(56) References Cited

U.S. PATENT DOCUMENTS

| 2,489,870 | A | 11/1949 | Dzus |
| 4,011,602 | A | 3/1977 | Rybicki et al. |
| 4,263,904 | A | 4/1981 | Judet |
| 4,590,928 | A | 5/1986 | Hunt et al. |
| 4,858,603 | A | 8/1989 | Clemow et al. |
| 4,878,794 | A | 11/1989 | Potucek |
| 4,898,186 | A | 2/1990 | Ikada et al. |
| 5,108,395 | A | 4/1992 | Laurain |
| 5,487,744 | A | 1/1996 | Howland |

(Continued)

FOREIGN PATENT DOCUMENTS

| WO | WO2011040986 | 4/2011 |
| WO | WO2012009162 | 1/2012 |

OTHER PUBLICATIONS

Orthopedics; Interfacet Distance and Facet Arthrosis: Dec. 2009 vol. 32 . No. 12.

(Continued)

*Primary Examiner* — Samuel Hanna
(74) *Attorney, Agent, or Firm* — Maywood IP Law; David Meibos; Barbara Daniels

(57) ABSTRACT

Eccentrically shaped bone fixation implants interact with bone fragments or joints to compress the bone fragments or joint bones together. The eccentrically shaped bone fixation implants can have longer and shorter portions along an axis and a plurality of teeth with opposing beveled surfaces in different configurations to vary both the direction and amplitude of the compressive forces applied to the bone fragments or joint bones. Instrumentation for implanting and orienting the eccentrically shaped bone fixation implants are also disclosed herein.

8 Claims, 21 Drawing Sheets

(56) References Cited

U.S. PATENT DOCUMENTS

| | | | |
|---|---|---|---|
| D368,777 S | 4/1996 | Goble et al. | |
| D374,286 S | 10/1996 | Goble et al. | |
| D374,287 S | 10/1996 | Goble et al. | |
| D374,482 S | 10/1996 | Goble et al. | |
| 5,681,311 A | 10/1997 | Foley et al. | |
| 6,123,711 A | 9/2000 | Winters | |
| 6,248,108 B1 | 6/2001 | Törmälä et al. | |
| 6,280,443 B1 | 8/2001 | Gu et al. | |
| 6,610,091 B1 | 8/2003 | Riley | |
| 6,648,893 B2 | 11/2003 | Dudasik | |
| 6,723,095 B2 | 4/2004 | Hammerslag | |
| 6,808,526 B1 | 10/2004 | Magerl et al. | |
| 6,811,567 B2 | 11/2004 | Reiley et al. | |
| 6,923,814 B1 | 8/2005 | Hildebrand et al. | |
| 6,945,975 B2 | 9/2005 | Dalton | |
| 6,979,333 B2 | 12/2005 | Hammerslag | |
| 7,090,675 B2 | 8/2006 | Songer | |
| 7,101,398 B2 | 9/2006 | Dooris et al. | |
| 7,563,275 B2 | 7/2009 | Falahee | |
| 7,608,094 B2 | 10/2009 | Falahee | |
| 7,699,878 B2 | 4/2010 | Pavlov et al. | |
| 7,708,761 B2 | 5/2010 | Petersen | |
| 7,744,630 B2 | 6/2010 | Lancial | |
| 7,749,251 B2 | 7/2010 | Obenchain | |
| 7,799,057 B2 | 9/2010 | Hudgins et al. | |
| 7,837,713 B2 | 11/2010 | Petersen | |
| 7,909,826 B2 | 3/2011 | Serhan et al. | |
| 8,002,799 B2 | 8/2011 | Chin et al. | |
| 8,043,343 B2 | 10/2011 | Miller et al. | |
| 8,585,744 B2 | 11/2013 | Duggal | |
| 2005/0192580 A1 | 9/2005 | Dalton | |
| 2005/0197700 A1 | 9/2005 | Boehm | |
| 2005/0240188 A1 | 10/2005 | Chow et al. | |
| 2006/0064099 A1 | 3/2006 | Pavlov et al. | |
| 2006/0190081 A1 | 8/2006 | Kraus et al. | |
| 2006/0217715 A1* | 9/2006 | Serhan et al. | 606/61 |
| 2006/0247632 A1* | 11/2006 | Winslow et al. | 606/61 |
| 2006/0293663 A1* | 12/2006 | Walkenhorst et al. | 606/61 |
| 2007/0250166 A1 | 10/2007 | McKay | |
| 2008/0177334 A1 | 7/2008 | Stinnette | |
| 2008/0234758 A1 | 9/2008 | Fisher et al. | |
| 2008/0255622 A1* | 10/2008 | Mickiewicz et al. | 606/319 |
| 2008/0255666 A1 | 10/2008 | Fisher et al. | |
| 2009/0036927 A1 | 2/2009 | Vestgaarden | |
| 2009/0082875 A1 | 3/2009 | Long | |
| 2009/0192551 A1 | 7/2009 | Cianfrani et al. | |
| 2009/0312763 A1 | 12/2009 | McCormack et al. | |
| 2009/0312800 A1* | 12/2009 | Chin | A61B 17/1757 606/279 |
| 2010/0069965 A1 | 3/2010 | Abdou | |
| 2010/0094356 A1 | 4/2010 | Varela et al. | |
| 2010/0280555 A1 | 11/2010 | Aflatoon et al. | |
| 2011/0182693 A1* | 7/2011 | Helgerson et al. | 411/337 |
| 2011/0190821 A1 | 8/2011 | Chin | |
| 2011/0245877 A1 | 10/2011 | Pisharodi | |
| 2012/0010658 A1* | 1/2012 | Kirschman | A61B 17/7064 606/246 |
| 2012/0010662 A1* | 1/2012 | O'Neil et al. | 606/279 |
| 2012/0010669 A1* | 1/2012 | O'Neil | A61B 17/7064 606/305 |
| 2012/0116454 A1 | 5/2012 | Edidin | |

OTHER PUBLICATIONS

Medco Forum; Percutaneous Lubmar Fixation Via Perpos PLS System From Interventional Spine: vol. 15 No. 37 Sep. 2008.

Medco Forum; Percutaneous Lumbar Fixation via Perpos PLS System from Interventional Spine: vol. 16 No. 49 Oct. 2009.

Interventional Spine; Bone Lock: Product Brochure, 2009 PN 7320 Rev. C DCR 837.

Concero; Facet Screw System Website WWW.lanx.com Jun. 30, 2011 @ 8:09 am MT.

Chin, Kingsley R; Early Results of the Triage Medical Percutaneous Transfacet Pedicular Bone-Lok Compression Device for Lubmbar Fusion: 5008 Rev. B, DCR 628.

SpineFrontier; FacetFuse, Chameleon MIS Screw System; Website, www.spinefrontier.com.

Medco Forum; Perpos PLS System from Interventional Spine, vol. 16, No. 61 Nov. 2009.

Mahar, Andrew; Journal of Spinal Disorders Technology: Biomechanical Comparison of a Novel Percutaneous Transfacet Device and a Traditional Posterior System for Single ;Level Fusion, vol. 19, No. 8, Dec. 2006.

Amedica; Javelin: MIS Locking Facet System, www.amedica.com Oct. 21, 2011 @ 3:05 pm MT.

Life Spine; FS3 Facet Screw Spinal System: www.lifespine.com Jun. 21, 2011 @ 12:18 pm MT.

Transl; Lumbar Fusion Vectre; www.transl.com Jun. 27, 2011 @ 10:03 am MT.

Amendia; Spartan Facet Screw www.amendia.com May 24, 2012 @ 9:17 am.

Spineology; Capture Facet Screw: Apr. 2010 Rev. F.

US Spine; Facet Bolt Design: www.us-spine.com.

X-spine Systems, Inc; Fixcet: www.x-spine.com Jun. 30, 2011 @ 8:32 am.

Globus Medical; Zyfuse: www.globusmedical.com Jun. 30, 2011 9:23 am MT.

* cited by examiner

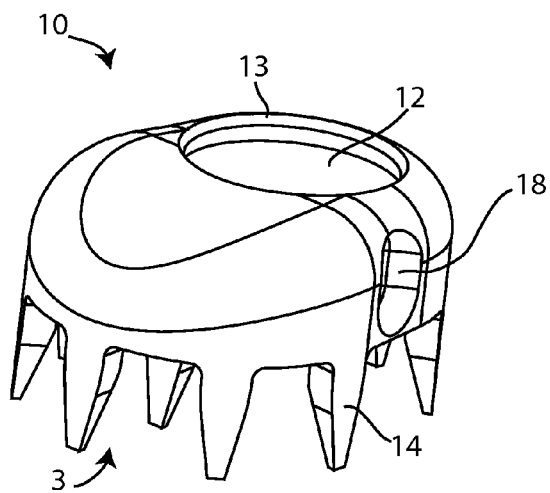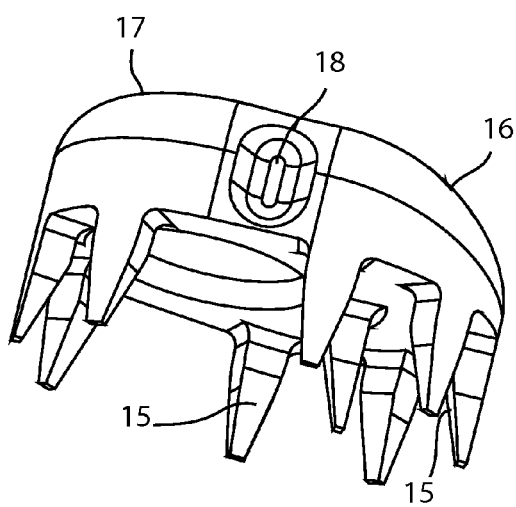
Fig. 1A     Fig. 1B
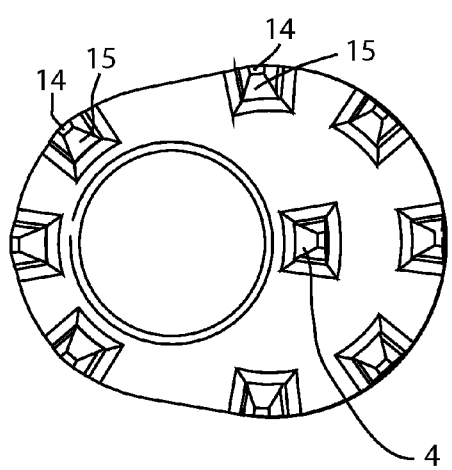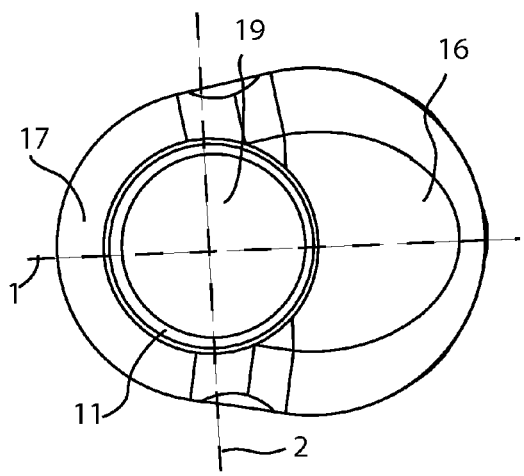
Fig. 1C     Fig. 1D

JOINT AND BONE FIXATION

CROSS-REFERENCE TO RELATED APPLICATIONS

This application claims the benefit of:

U.S. Provisional Patent Application No. 61/554,218 which was filed Nov. 1, 2011, entitled: SYSTEMS AND METHODS FOR FACET FIXATION.

The above-identified document is herein incorporated by reference in its entirety.

BACKGROUND

The present disclosure relates to bone and joint fixation and instrumentation and methods for preparation and implantation of these devices. Joint fixation may be necessary in cases of pain and inflammation due to cartilage degeneration, nerve impingement, spinal misalignment, and motion instability. The primary examples described herein illustrate how this concept is applied to the facet joint, but this concept applies equally to other joints where similar causes of pain and inflammation are indicated. Those of skill in the art will recognize that the following description is merely illustrative of the principles of the disclosure, which may be applied in various ways to provide many different alternative embodiments and may be applicable outside the fields of surgery or medical devices. While the present disclosure is made in the context of facet joints in the lumbar spinal region for the purposes of illustrating the concepts of the design, it is contemplated that the present design and/or variations thereof may be suited to other uses, such as cervical facet joints, thoracic facet joints, other joints in the human body, or to stabilize bone fractures, etc. Moreover, the implants, instrumentation and methods set forth herein may be used in open, percutaneous, and/or minimally invasive procedures and may be placed via intra-facet, trans-facet, trans-laminar, or trans-pedicle means.

All changes which come within the meaning and range of equivalency of the claims are to be embraced within their scope.

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

BRIEF DESCRIPTION OF THE DRAWINGS

Various embodiments of the present disclosure will now be discussed with reference to the appended drawings. It will be appreciated that these drawings depict only typical examples of the present disclosure and are therefore not to be considered limiting of its scope.

FIG. 1A is an isometric view of a cap in accordance with one example of the present disclosure;

FIG. 1B is a bottom isometric view of the cap in FIG. 1A;

FIG. 1C is a bottom view of the cap in FIG. 1A;

FIG. 1D is a top view of the cap in FIG. 1A;

DETAILED DESCRIPTION

While certain embodiments are shown and described in detail below by way of illustration only, it will be clear to the person skilled in the art upon reading and understanding this disclosure that changes, modifications, and variations may be made and remain within the scope of the technology described herein. Furthermore, while various features are grouped together in the embodiments for the purpose of streamlining the disclosure, it is appreciated that features from different embodiments may be combined to form additional embodiments which are all contemplated within the scope of the disclosed technology.

Not every feature of each embodiment is labeled in every figure in which that embodiment appears, in order to keep the figures clear. Similar reference numbers (for example, those that are identical except for the first numeral) may be used to indicate similar features in different embodiments.

Any of the devices described herein may be fabricated from metals, alloys, polymers, plastics, ceramics, glasses, composite materials, or combinations thereof, including but not limited to: PEEK, titanium, titanium alloys, commercially pure titanium grade 2, ASTM F67, Nitinol, cobalt chrome, stainless steel, UHMWPE, and biodegradable materials, among others. Different materials may be used within a single part. The implants disclosed herein may also encompass a variety of surface treatments or additives to encourage bony attachment, including but not limited to: porous coatings, hydroxyapatite, TCP, anti-microbial additives, analgesics, anti-inflammatories, BMP's, PMA material, bone growth promoting material, PLLA (poly-L-lactide), PGA (polyglycolide), TCP (tricalcium phosphate), demineralized bone, cancellous bone chips, etc. Any implant disclosed herein may include a radiographic marker for imaging purposes. Any implant disclosed herein may be colored, coded or otherwise marked to make it easier for the surgeon to identify the type and size of the implant.

Figure 1E:
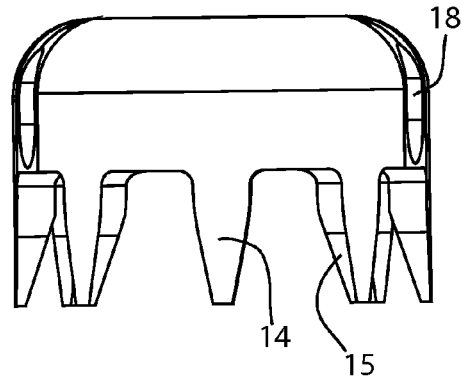
FIG. 1E is a back view of the cap in FIG. 1A.
Figure 1F:
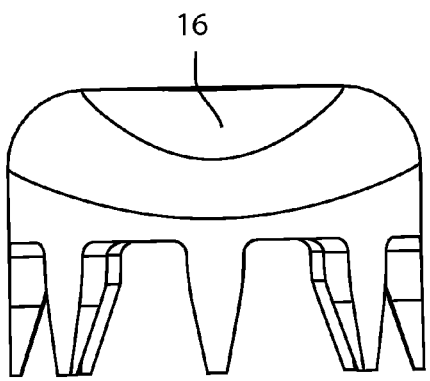
FIG. 1F is a front view of the cap in FIG. 1A.
Figure 1G:
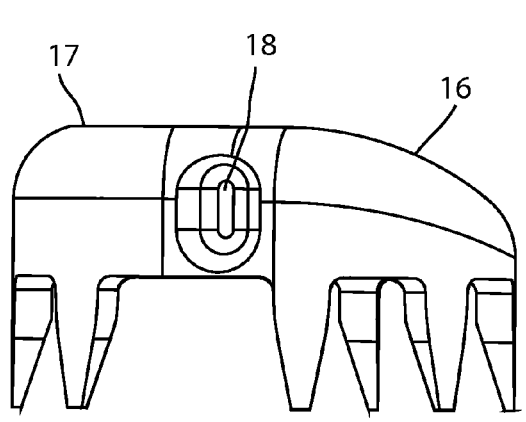
FIG. 1G is a left side view of the cap in FIG. 1A.
Figure 1H:
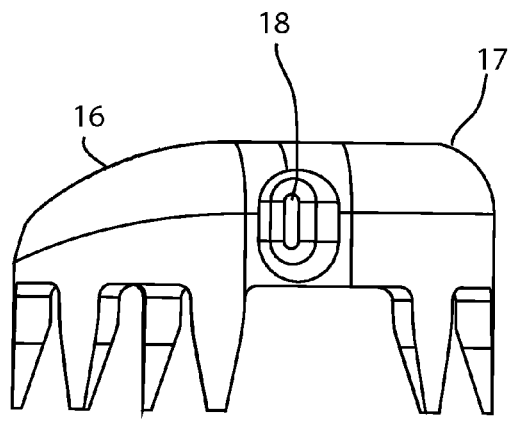
FIG. 1H is a right side view of the cap in FIG. 1A.
Figure 2A:
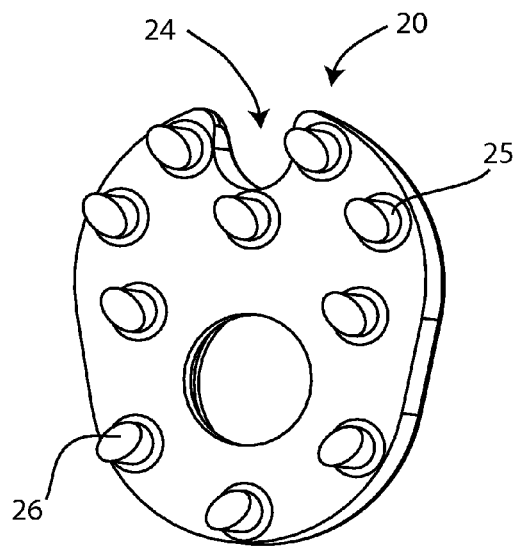
FIG. 2A is an isometric view of a cap in accordance with another example of the present disclosure.
Figure 2B:
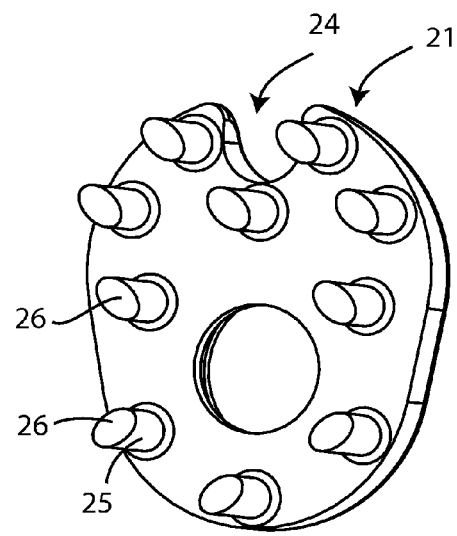
FIG. 2B is an isometric view of the cap in FIG. 2A with longer teeth.
Figure 2C:
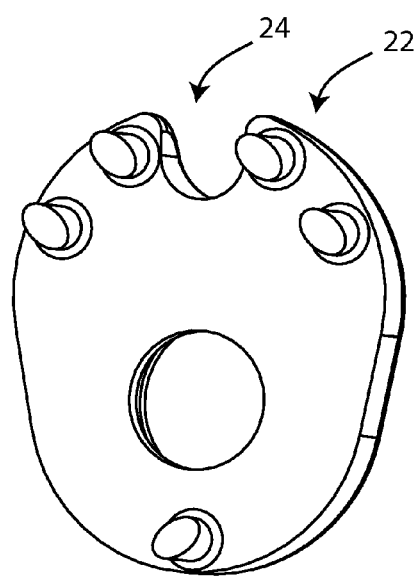
FIG. 2C is an isometric view of a cap in accordance with another example of the present disclosure.
Figure 2D:
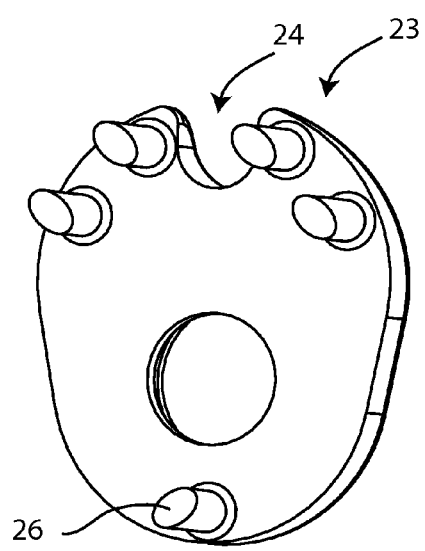
FIG. 2D is an isometric view of the cap of FIG. 2C with longer teeth.

FIGS. 1A-1H illustrate one example of a cap 10 useful for fixing a bone fracture or joint to provide stabilization. The cap 10 can have a first portion 16 and a second portion 17. Referring to FIG. 1D, the first portion 16 can be longer than the second portion 17 along a first axis 1 which intersects the first portion, the second portion, and an aperture 19 formed in the cap 10. In some examples, the first portion 16 may also be longer then the second portion 17 along a second axis 2. This creates an eccentrically shaped cap 10 with the first portion 16 being asymmetrically shaped in comparison to the second portion 17. The shape of the cap 10 can also be referred to as "oblong" in some examples, with the first portion 16 forming a lobe that is larger than the second portion 17. The eccentric shape of the cap 10 allows a surgeon more freedom to orient the larger lobe portion across the joint to facilitate joint fixation and increases the load bearing area of the implant 10. In some examples, the cap 10 can also curve downward to create a lower profile implant. For example, FIGS. 1G and 1H show left and right side views of the cap 10 with the first portion 16 of the cap curving downward.

The cap 10 can include one or more teeth 14 on a bone engaging side 3 of the cap 10. The plurality of teeth 14 can have beveled surfaces 15 that are arranged to at least partially oppose each other between the first portion 16 of the cap 10 and the second portion 17 of the cap 10. The beveled surfaces 15 can be made to diverge away from each other in the superior to inferior direction and converge toward each other in the inferior to superior direction. In this manner, the beveled surfaces 15 can act to compress the joint bones together as the teeth 14 are driven into the bones. The angle of the beveled surfaces 15 can be adjusted to increase or decrease the compressive forces created by the cap 10. For example, if the angle of the beveled surfaces 15 is increased, the teeth can impart a greater compressive force for a given distance that the teeth 14 are driven into the bones. Thus, the size, length, bevel shape, bevel angle, and distribution of the teeth may vary in any of the examples disclosed herein. For example, the number and spacing of the teeth 14 can be chosen to maximize the fixation properties of the cap 10 in view of the size and condition of the joint bones of the patient. In some examples, the teeth 14 can be distributed on the bone engaging side 3 of the cap 10 along the outer perimeter of the bone engaging side 3 of the cap 10. In other examples the teeth 14 can be distributed away from the outer perimeter of the bone engaging side 3 of the cap 10. For example, FIG. 1C has a tooth 4 which does not lie along the outer perimeter of the bone engaging side 3 of the cap 10, rather tooth 14 is located deeper within the interior of the first portion 16. Having teeth distributed in this manner can increase the bone grabbing performance of the implant by increasing the number of teeth within the interior of the first portion 16.

Figure 5A:
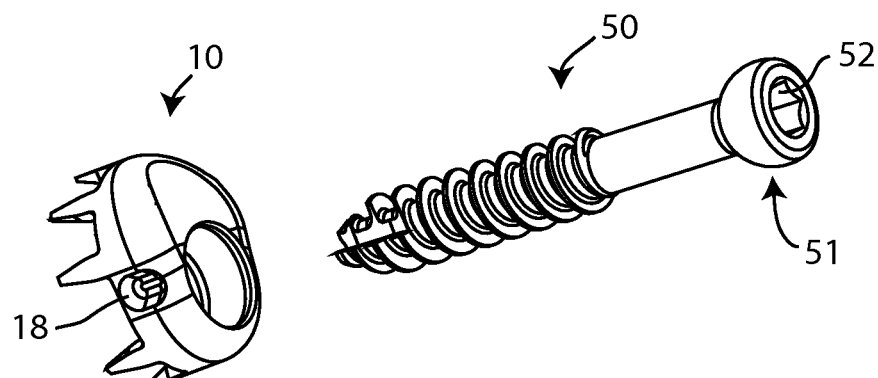
FIG. 5A shows a cap and fastener before they are assembled together.
Figure 5B:
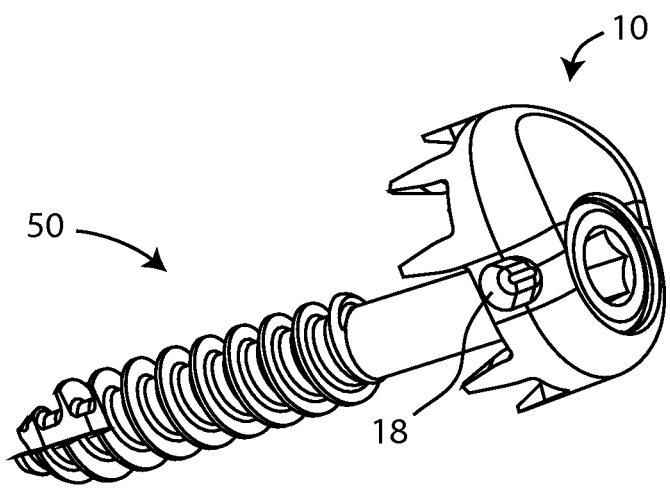
FIG. 5B shows a cap and fastener assembly after they are assembled together.
Figure 6:
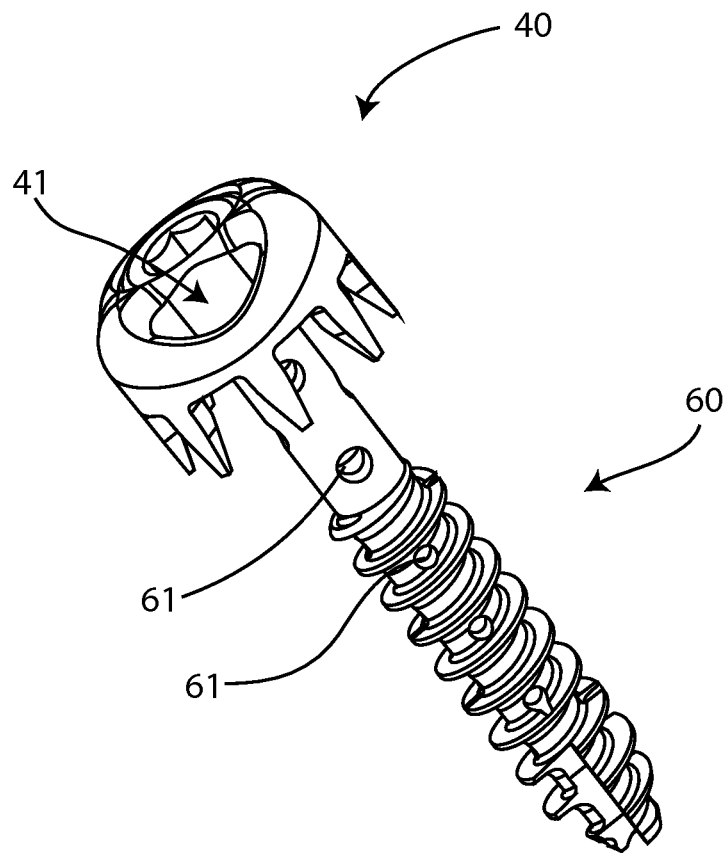
FIG. 6 shows a cap and fastener assembly according to another example of the present disclosure.

Continuing with FIGS. 1A and 1D, the cap 10 can have an aperture 19 formed through the cap 10 and configured to receive a suitable fastener 50, as can be seen in FIGS. 5A-6. The shaft of the fastener 50 may be partially threaded to promote compression. The fastener 50 can also be self-tapping (or self-threading) and may be cannulated down its center so that it can be placed into the facet joint with a K-wire. The cap 10 can have a chamfered spherical capsule 12 shaped to receive a complimentarily shaped partially spherical fastener head 51, as shown in FIG. 5A. This allows the fastener 50 to rotate within the aperture 19 and concentrically pivot along its longitudinal axis to ensure that the cap 10 can align itself with the joint bones as the cap 10 is forced into the joint bones. The aperture 19 can also be deep enough to allow the fastener head 51 to be recessed within the aperture 19 to provide a smooth, low profile implant. A smooth, low profile implant can help reduce irritation to surrounding soft tissue. The aperture 19 may also be encircled by a lip 13 which projects inward and has a diameter slightly smaller in size than the diameter of the head portion 51 of the suitable fastener 50. This can allow the fastener to be "press fit" into the aperture such that the lip 13 provides an interference that captures the fastener 50 within the aperture 19. The lip 13 can be flush with the surrounding surface of the implant to avoid any abrupt changes in the shape of the implant resulting in smooth surfaces. Thus, the smooth lip 13 that sits flush with the surrounding surface will help reduce irritation to surrounding soft tissues, as compared to other interference fit configurations, such as collet style interference structures which have multiple slits and protruding structures that can cause interference and irritation to surrounding soft tissues and bones.

Figure 3:
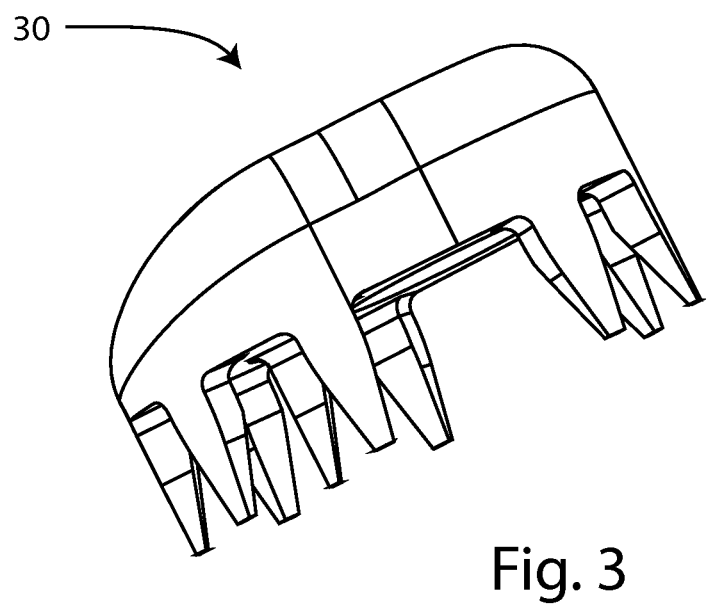
FIG. 3 is an isometric view of a cap in accordance with another example of the present disclosure.

Continuing with FIGS. 1A-1H, the cap 10 can have one or more slots 18 formed in a surface of the cap 10. The slots 18 can interact with a guide tool to hold the cap 10 in a specific orientation during insertion. In other examples, the cap 10 may not include one or more slots 18 formed in a surface of the cap 10. One such example can be seen in FIG. 3.

FIGS. 2A-2D illustrate alternative examples of caps 20, 21, 22, and 23 which can be used to fix bones or joints according to other examples of the present disclosure. Each of the caps 20, 21, 22, and 23 may include one or more slots 24 configured to interact with a guide tool to hold the cap at a specific orientation during insertion. However, in other examples, the cap may not include one or more slots 24. It will be appreciated that the location of the one or more slots 24 around the perimeter of the caps may vary, as may the size, diameter and/or number of the one or more slots 24. The one or more slots 24 may cooperate with a suitable guide for properly aligned placement of the cap into the joint, as will be discussed in greater detail below. The caps 20, 21, 22, and 23 can also include a plurality of teeth 25 that can be cylindrical in shape and have varying lengths. The teeth 25 can also include opposing beveled surfaces 26 similar to other embodiments disclosed herein.

Figure 4:
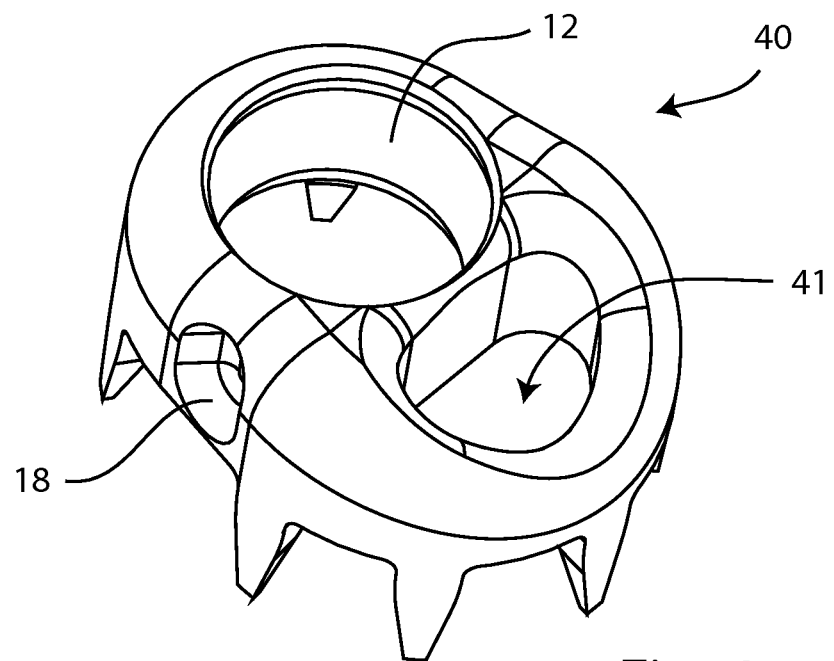
FIG. 4 is an isometric view of a cap in accordance with another example the present disclosure.

Referring now to FIG. 4, a cap 40 is shown with an aperture or fenestration 41 formed through the cap 40 and configured to promote bone growth, or bone fusion, by providing a graft pocket for material such as bone chips or bone growth promoters. FIG. 6 illustrates the cap 40 in combination with a faster 60, which is also fenestrated with apertures 61 throughout the fastener 60 which can also be packed with bone chips or bone growth promoters. This combination may further promote bony ingrowth and bone fusion between the faster 60, the cap 40, and the bones.

Figure 7A:
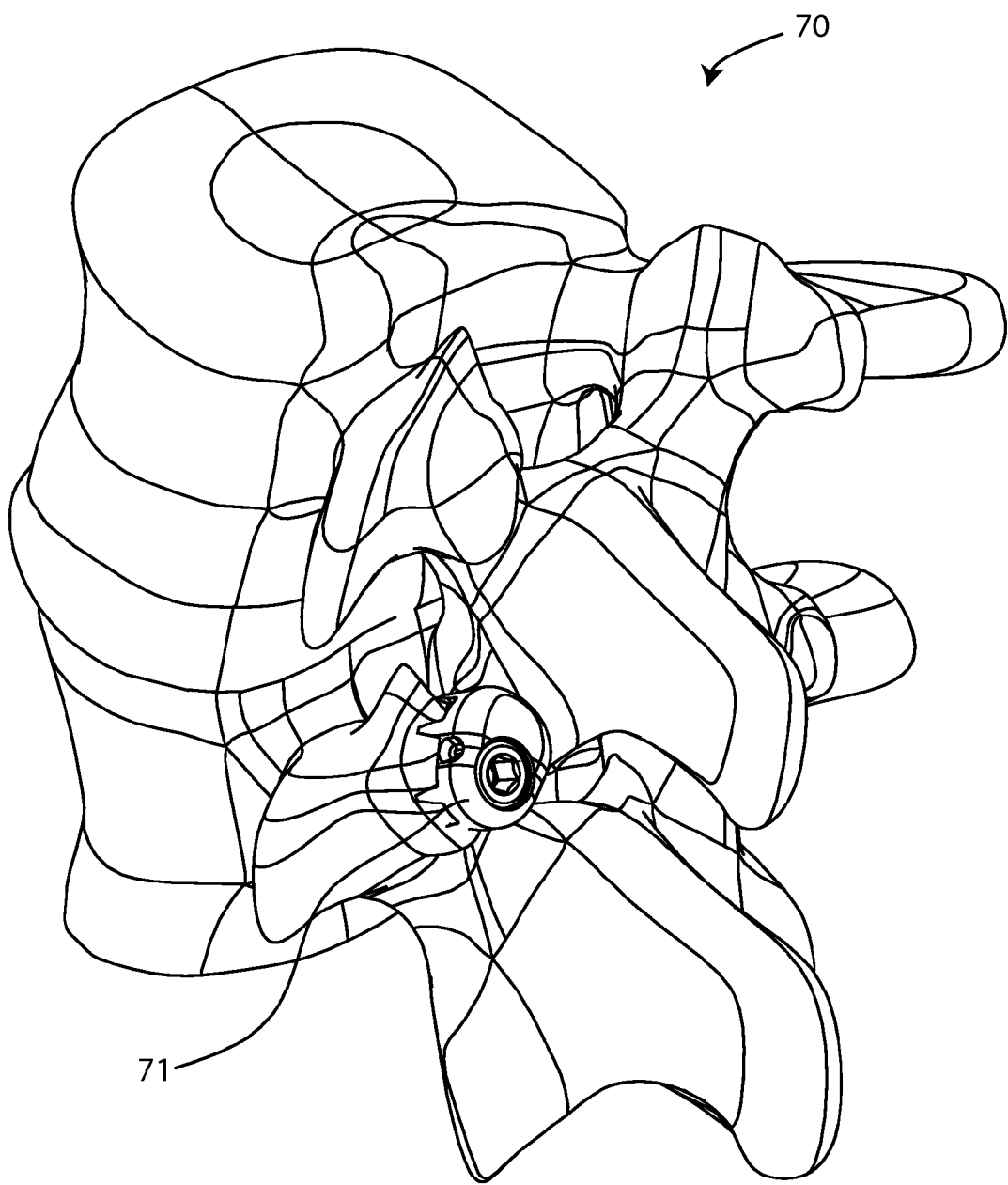
FIG. 7A shows a portion of a spine with an implant fastened to a facet joint according to the present disclosure.
Figure 7B:
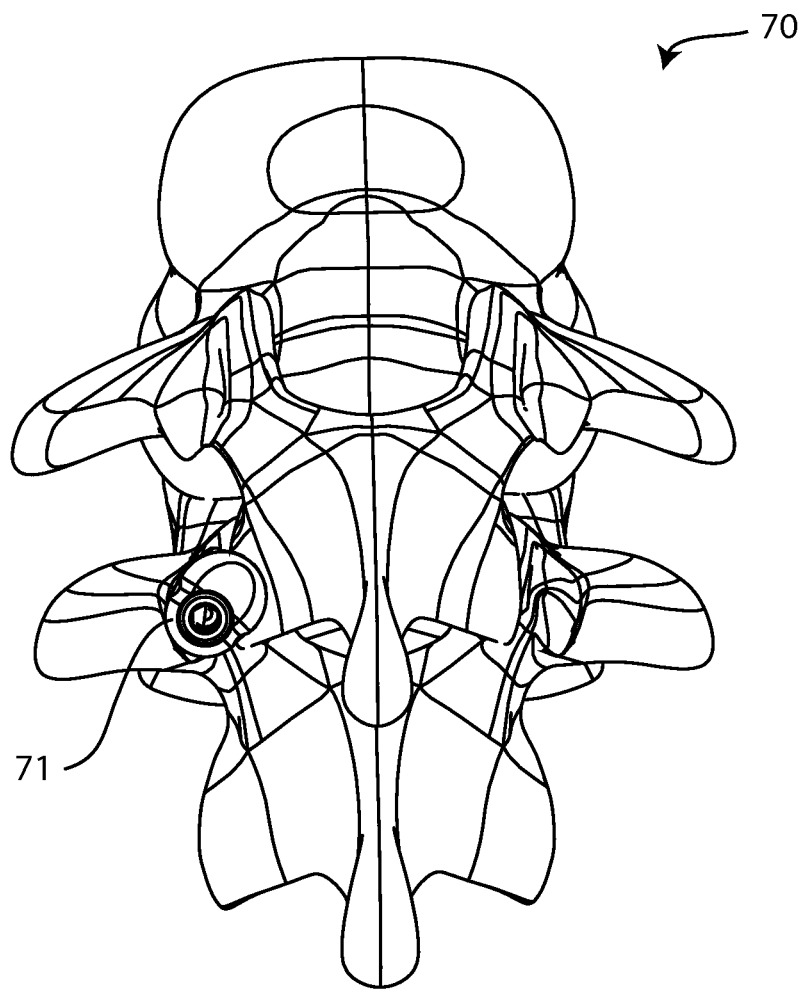
FIG. 7B shows a back isometric view of the spine and implant of FIG. 7A.
Figure 8A:
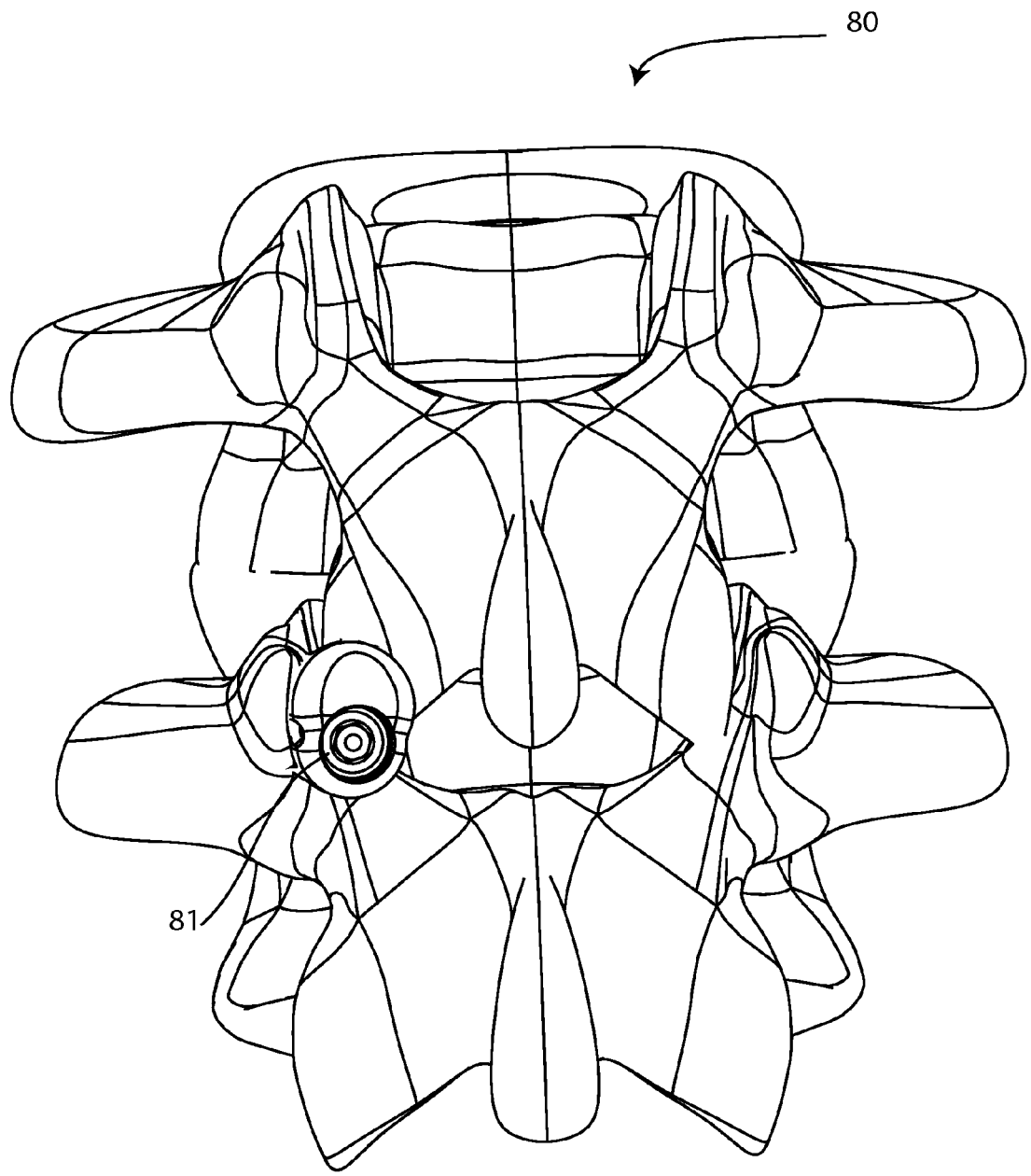
FIG. 8A shows an isometric view of a portion of a spine with an implant fastened to a facet joint in a first orientation.
Figure 8B:
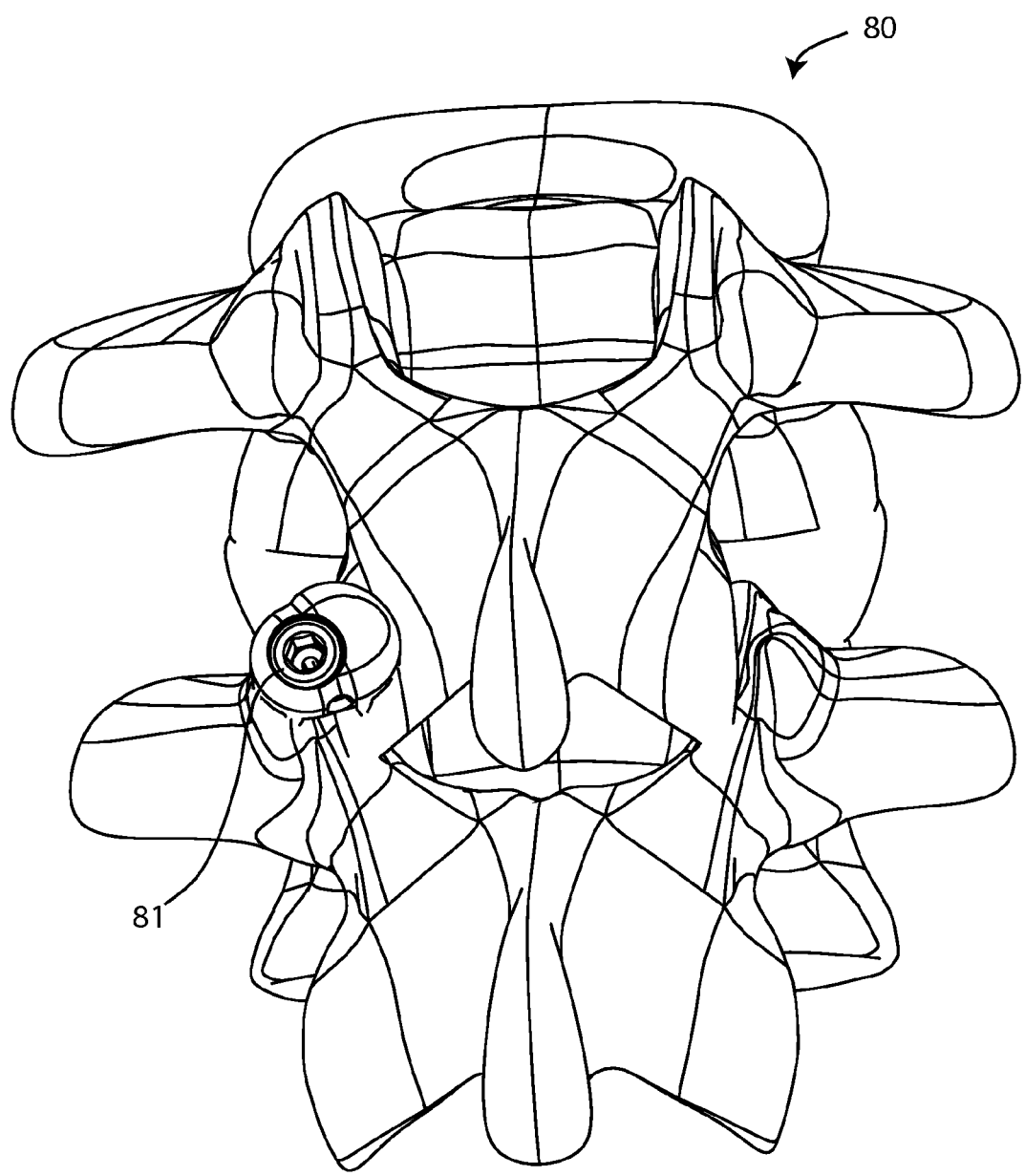
FIG. 8B shows an isometric view of a portion of a spine with an implant fastened to a facet joint in a second orientation.
Figure 8C:
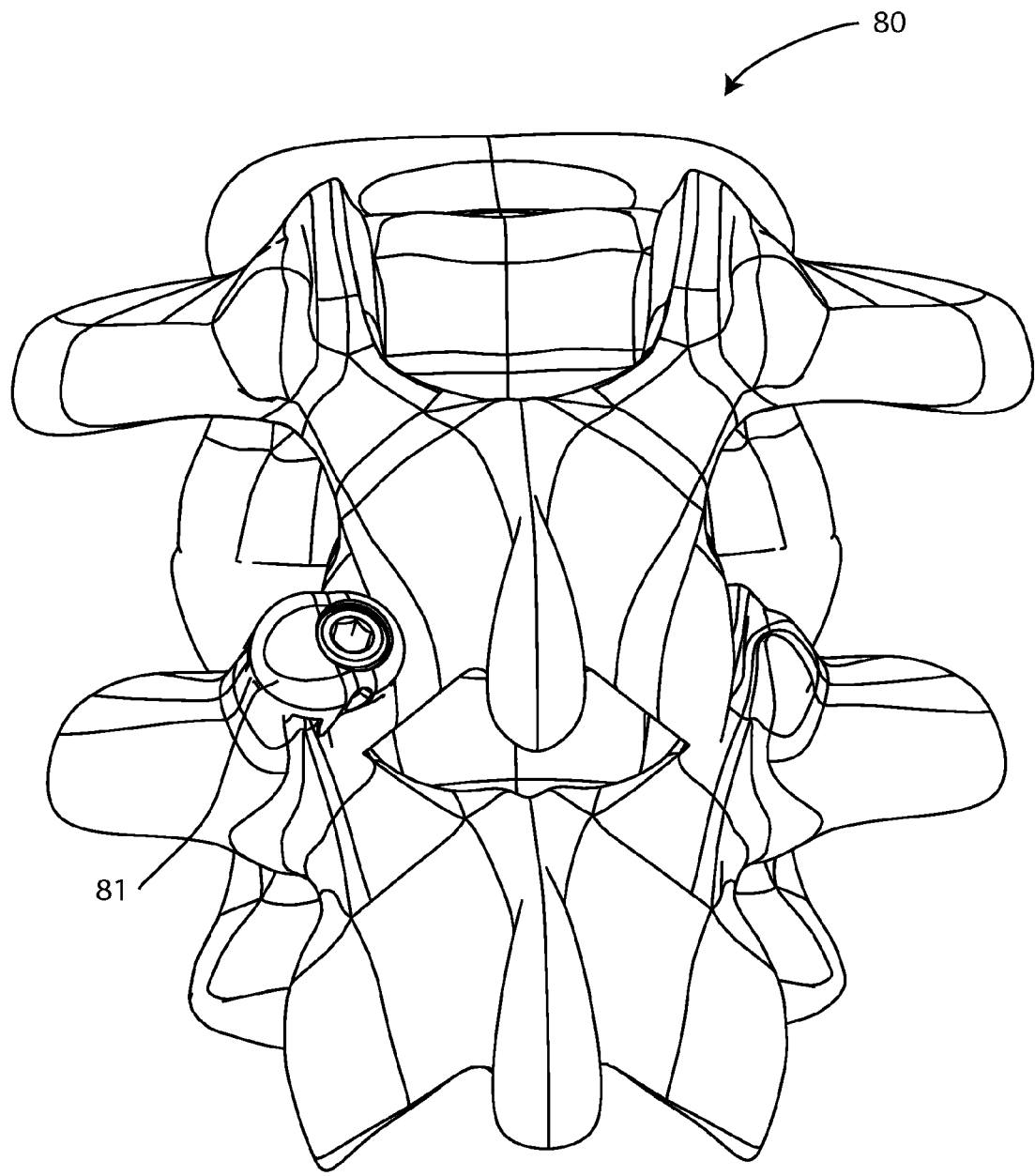
FIG. 8C shows an isometric view of a portion of a spine with an implant fastened to a facet joint in a third orientation.
Figure 8D:
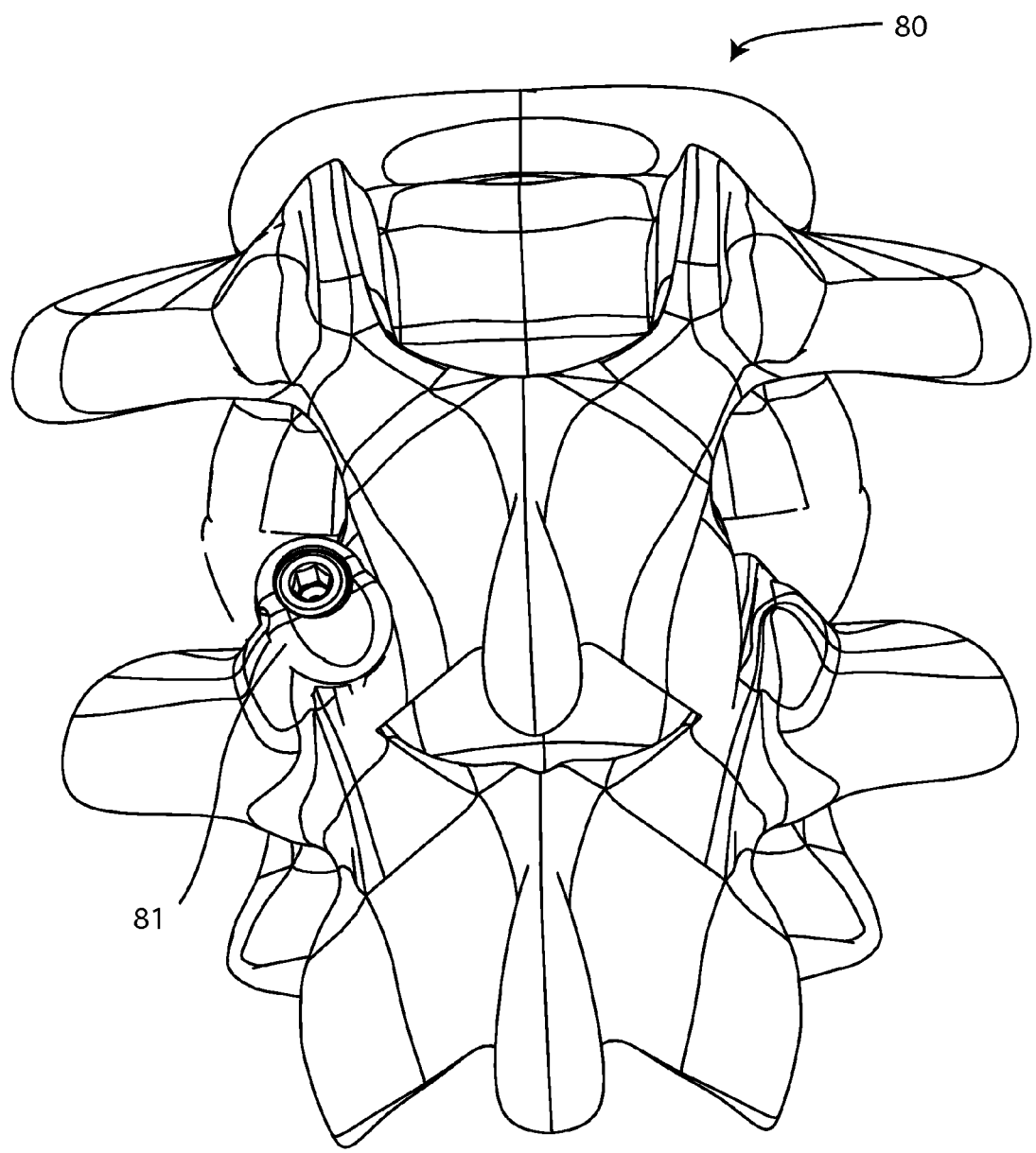
FIG. 8D shows an isometric view of a portion of a spine with an implant fastened to a facet joint in a fourth orientation.
Figure 8E:
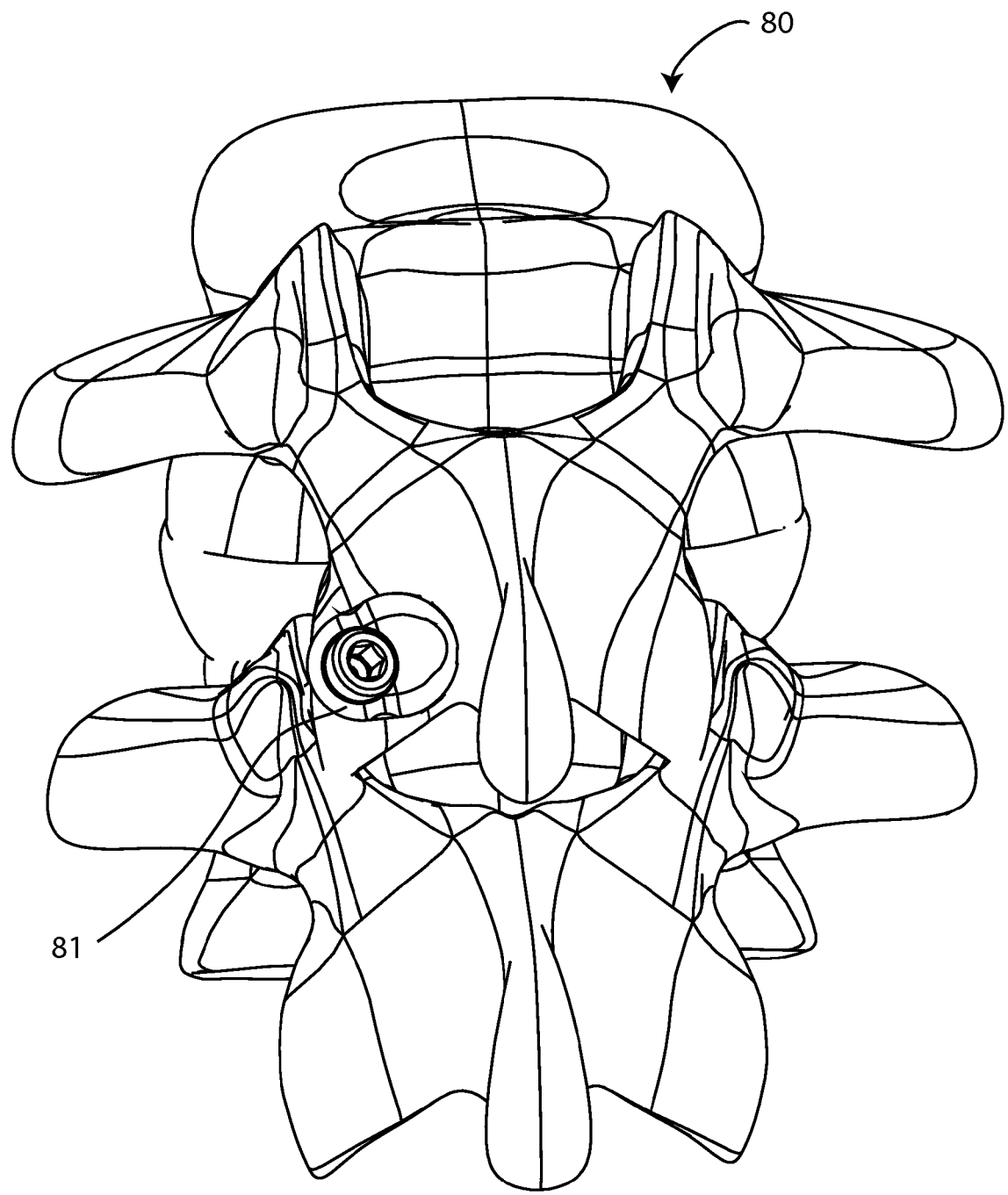
FIG. 8E shows an isometric view of a portion of a spine with an implant fastened to a facet joint in a fifth orientation.
Figure 9:
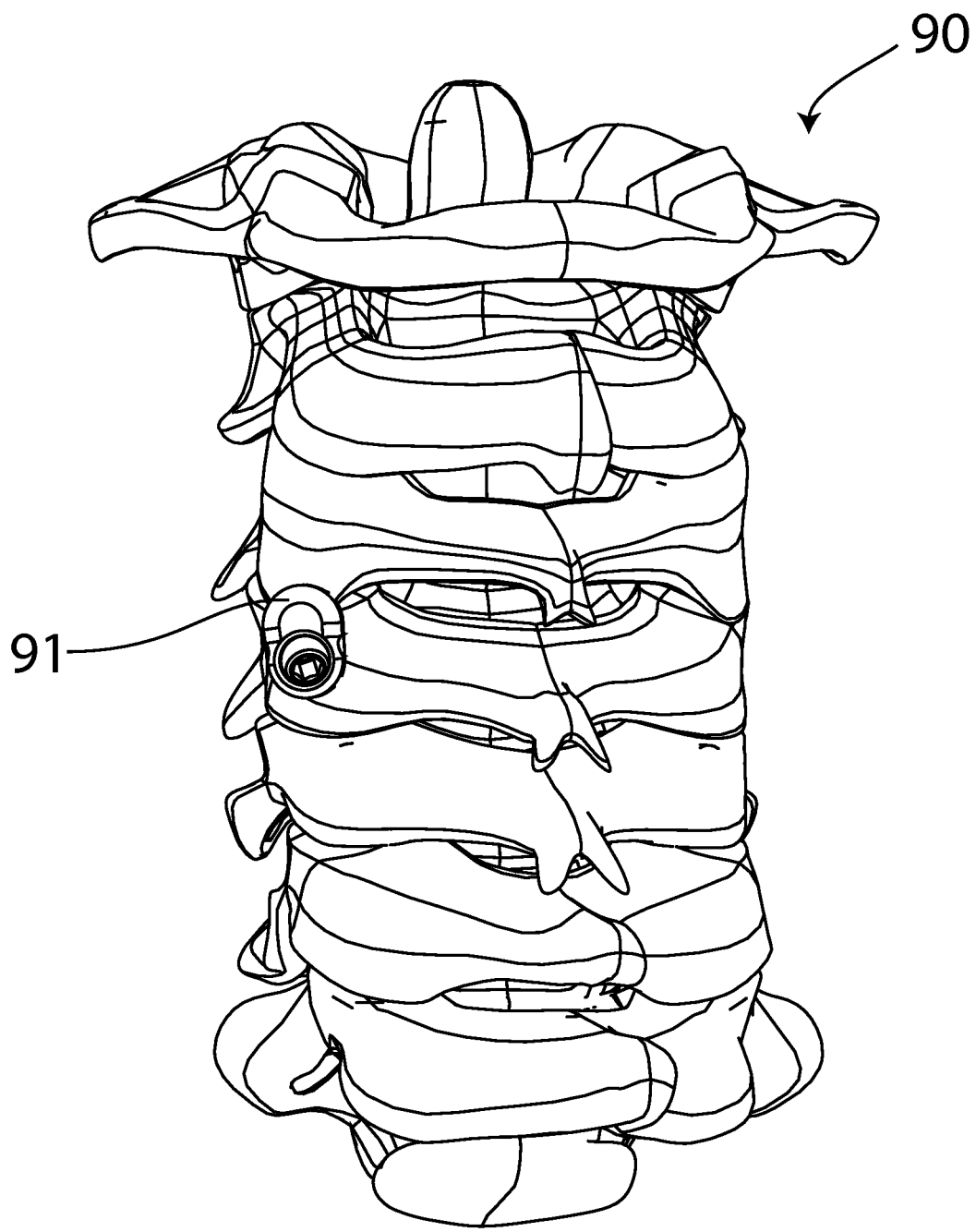
FIG. 9 shows a portion of a cervical spine with an implant fastened to a facet joint according to the present disclosure.

FIGS. 7-9 show various implants affixed to facet joints in portions of the spine. FIG. 7A shows an isometric view of an implant 71 affixed to a facet joint in a lumbar portion of a spine 70. FIG. 7A shows a back isometric view of the implant 71 affixed to the lumbar portion of the spine 70 in FIG. 7.

FIGS. 8A-8E show examples of various placement options for an implant 81 in a portion of a spine 80, all of which are easily achievable with the guides and instrumentation disclosed herein. FIG. 8A shows the cap 81 with the fastener piercing the lower or inferior part of the superior articular process and the lobe of the cap oriented superiorly to capture the inferior articular process with the lobe of the cap 81. FIG. 8B shows the cap 81 with the fastener piercing the lateral or middle part of the superior articular process and the lobe of the cap oriented medially to capture the inferior articular process with the lobe of the cap 81. FIG. 8C shows the cap 81 with the fastener piercing the inferior articular process (transfacet) and the lobe of the cap is inverted or oriented laterally to capture the superior articular process with the lobe of the cap 81. FIG. 8D shows the cap 81 with the fastener piercing the upper or superior part of the superior articular process and the lobe of the cap is oriented inferiorly to capture the inferior articular process with the lobe of the cap 81. FIG. 8E shows the cap 81 with the fastener piercing the inferior articular process (transfacet) and the lobe of the cap 81 is oriented medially to capture the inferior articular process with the lobe of the cap 81.

FIG. 9 shows an isometric view of an implant 91 affixed to a facet joint in a cervical portion of the spine 90 demonstrating that the implants disclosed herein can be used in all portions of the spine as well as in other parts of the body.

Methods of inserting the implants disclosed herein will now be given. A K-wire can be inserted into the portion of the facet joint where the surgeon desires to affix the fastener to the facet joint. In one example, the K-wire can be inserted into the inferior facet joint and oriented such that the fastener will enter into the pedicle of the inferior facet joint.

Figure 10:
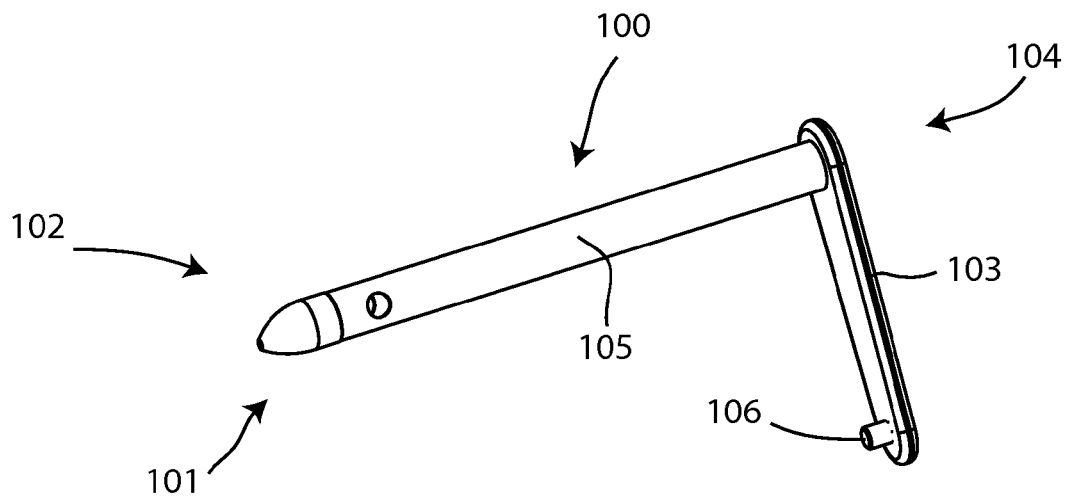
FIG. 10 shows an isometric view of a dilator in accordance with one example of the present disclosure.
Figure 11:
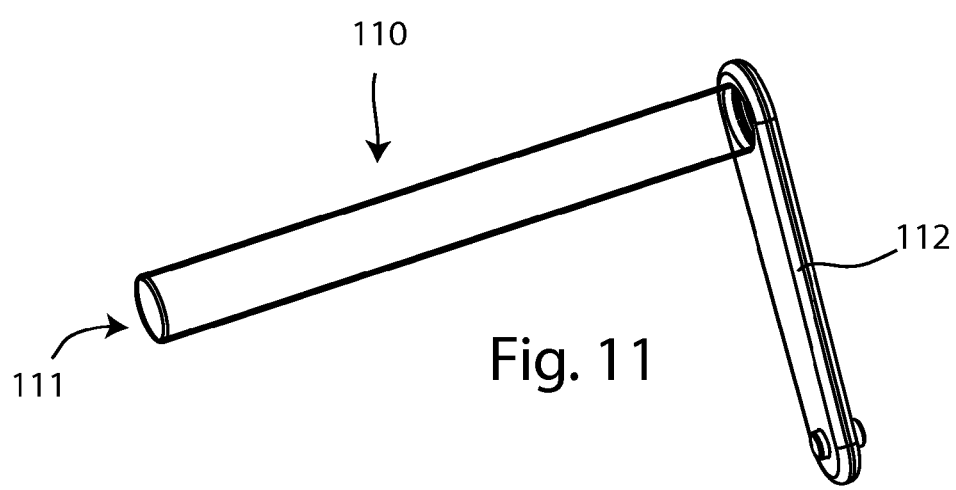
FIG. 11 shows an isometric view of a cannula in accordance with one example of the disclosure.
Figure 12:
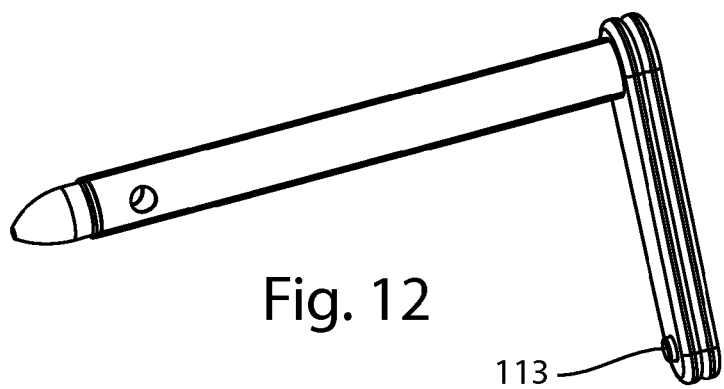
FIG. 12 shows the dilator of FIG. 10 inserted into the cannula of FIG. 11.

Once the K-wire is in the desired location, a dilator 100 and cannula 110 assembly can be threaded over the K-wire and inserted into the soft tissue of the patient to provide sufficient access to the facet joint. FIG. 10 shows an isometric view of a dilator 100 according to one example of the present disclosure. The dilator 100 can have a pointed tip 101 at its distal end 102 and a handle portion 103 at its proximal end 104. The dilator 100 can also have a shaft 105 having a diameter slightly less than the diameter of the hollow shaft 111 of a cannula 110 as seen in FIG. 11. The dilator 100 can be inserted into the cannula 110 as shown in FIG. 12, and the handles 103, 112 of the dilator 100 and the cannula 110 can also align with and engage each other via a boss 106 attached to the handle 103 of the dilator 100 and an aperture 113 formed in the handle 112 of the cannula 110.

Figure 13:
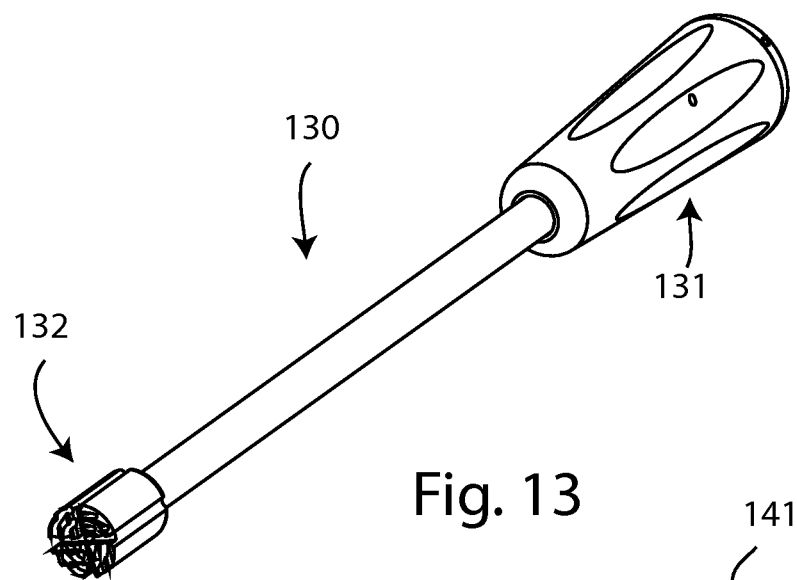
FIG. 13 shows an isometric view of a manual reamer in accordance with one example of the present disclosure.
Figure 14:
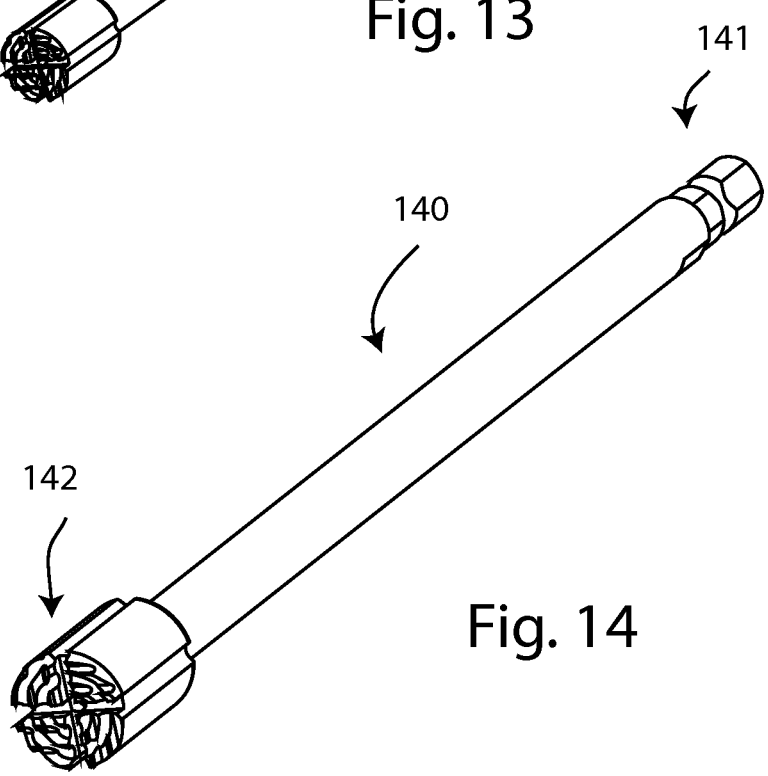
FIG. 14 shows an isometric view of a powered reamer in accordance with another example of the present disclosure.

Once the tissue is dilated, the surgeon can remove the dilator 100 from the cannula 110 thus exposing the facet joint through the cannula for the remainder of the surgery. The surgeon may then ream the bone surface of the facet joint with a suitable reamer 130, 140 to prepare the bone surface for receiving the implant. The reamer 130 shown in FIG. 13 is a manual reamer with a handle 131 and a reamer head 132. The reamer 140 shown in FIG. 14 is a powered reamer with a connection 141 configured to receive a suitable power tool and a reamer head 142.

Figure 15A:
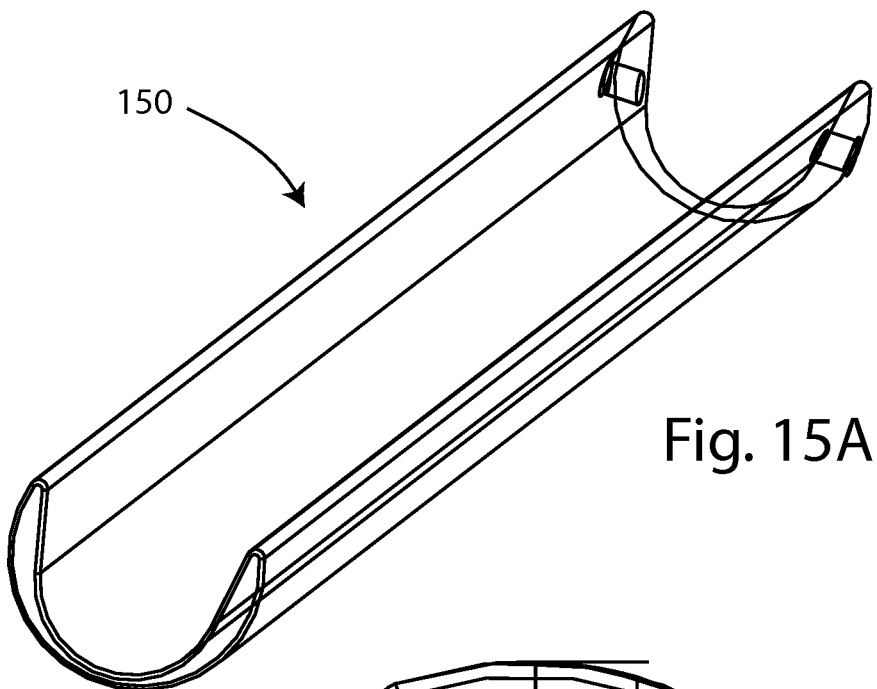
FIG. 15A shows an isometric view of a guide in accordance with one example the present disclosure.
Figure 15B:
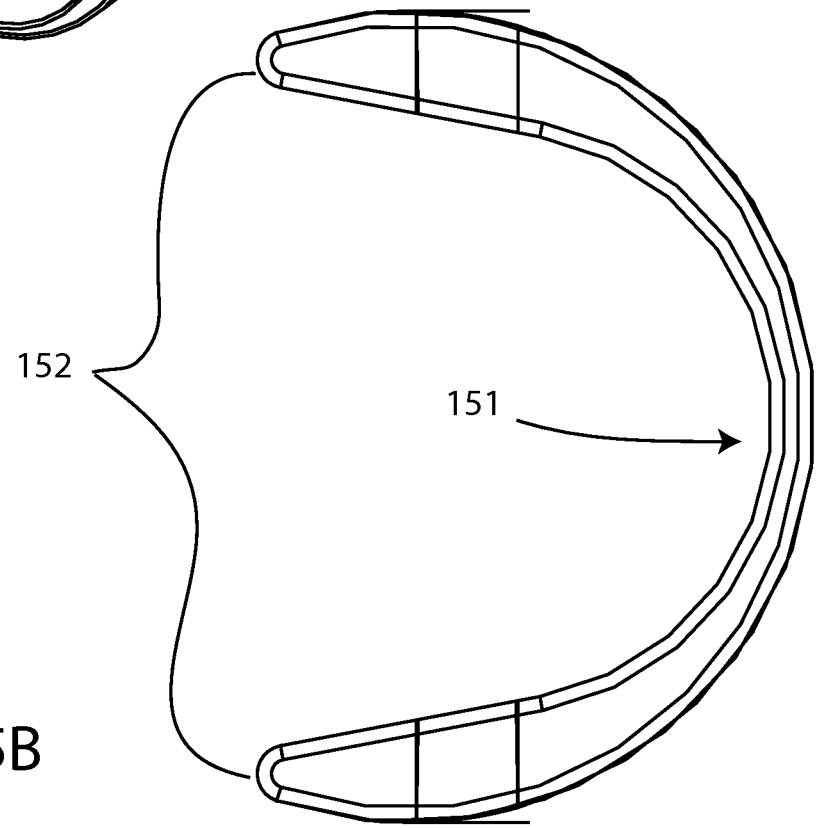
FIG. 15B shows a front view of the guide of FIG. 15A.

Once the implant site is sufficiently prepared to receive the implant, one or more guides can be used to orient and insert a suitable implant, as can be seen in FIGS. 15A-17C. FIGS. 15A-15B illustrate one example of a guide 150 that may be used with an implant 30 shown in FIG. 3. The implant 30 does not have any slots to engage a portion of the guide 150, as other embodiments disclosed herein. Rather, the guide 150 is shaped to receive the smaller second portion of the cap 30 in the smaller inner portion 151 of the guide 150 and the larger first portion of the cap 30 in the larger inner portion 152 of the guide 150, as is shown in the front view of the guide in FIG. 15B. The guide 150 is a semi-tubular or semi-cylindrical member. The outer diameter of the guide 150 may be round to complementarily fit within the cannula, but the inner diameter can have a unique cutout profile to accommodate the smaller-diameter end of the cap. In the example shown, the guide 150 may not be quite a half-pipe as it sweeps close to 245°. Other guide examples may vary in size and shape to accommodate the geometry of other cap embodiments. The inner diameters of the cannula 110 and guide 150 match the two different outer diameters of the cap 30. This provides control for proper placement of the cap 30. Thus, the guide 150 is shaped to cooperate with the asymmetrical or eccentric geometry of the cap 30 to guide the cap 30 into place. The guide 150 can be inserted into the cannula 110 and a cap 30 with a suitable fastener attached thereto can be affixed to a suitable driver 180, such as that shown in FIG. 18. The cap 30 can then be inserted into the guide and moved toward the implant site. The shape of the guide 150 in combination with the shape of the cannula 110 keeps the cap 30 in the proper orientation as the surgeon slides the cap 30 toward the implant site.

The driver 180 can have a hexagonal tip 181 configured to interact with a hexagonal aperture 52 as seen in FIG. 5A. The hexagonal aperture 52 can also be chamfered to help the driver 180 stay engaged with the fastener 50.

In one method of implantation, the cap 30 may be placed first, allowing the teeth to capture bone surfaces on both sides of the joint, followed by placement of the fastener 50 to provide compression and stability.

Figure 16:
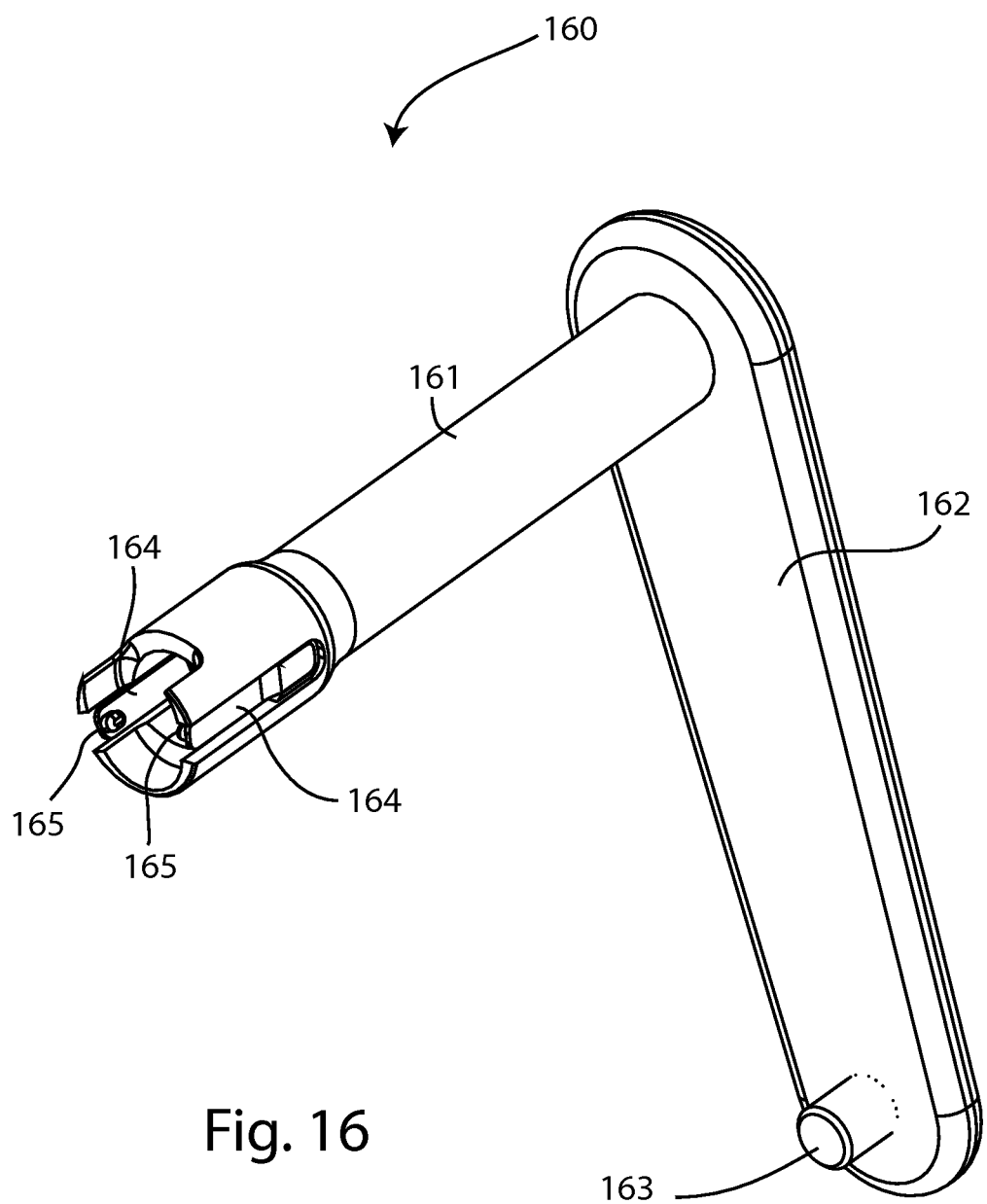
FIG. 16 shows an isometric view of a guide in accordance with another example the present disclosure.

FIG. 16 shows an alternative example of a guide for use with other implants described herein. The guide 160 can have a shaft 161 and a handle 162 with a boss attached to the handle 162. The shaft 161 can be hollow and can include one or more retaining members 164 engaged with the distal end of the hollow shaft 161. Moreover, the retaining members 164 can include boss members 165 sized and shaped to engage suitably shaped slots 18 formed in the cap 10. In other examples, the cap 10 may include other features to cooperate with the one or more retaining members 164, such as recesses, dimples, or grooves. The boss members 165 may be oriented to be offset from each other at the distal end of guide 160 in order to match the offset or eccentric shape of the slots 18 in the cap 10.

Figure 17A:
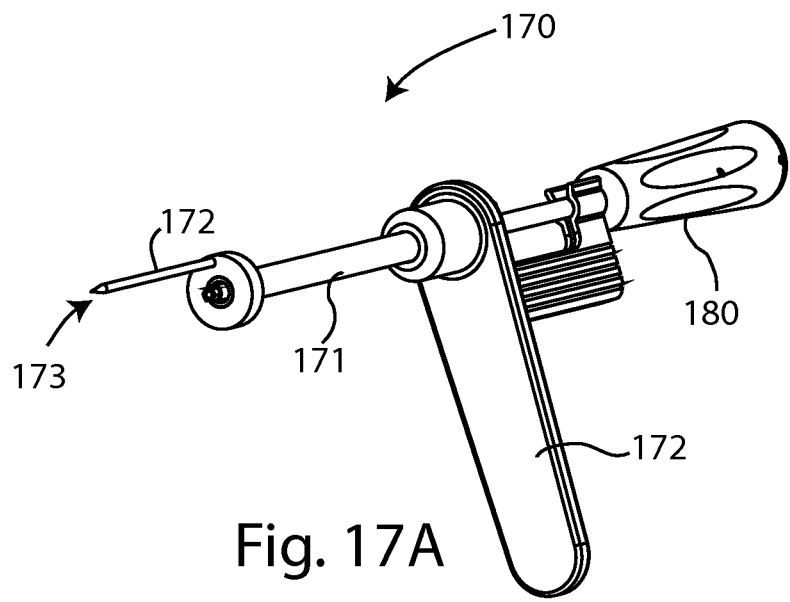
FIG. 17A shows an isometric view of a guide in accordance with another example the present disclosure.
Figure 17B:
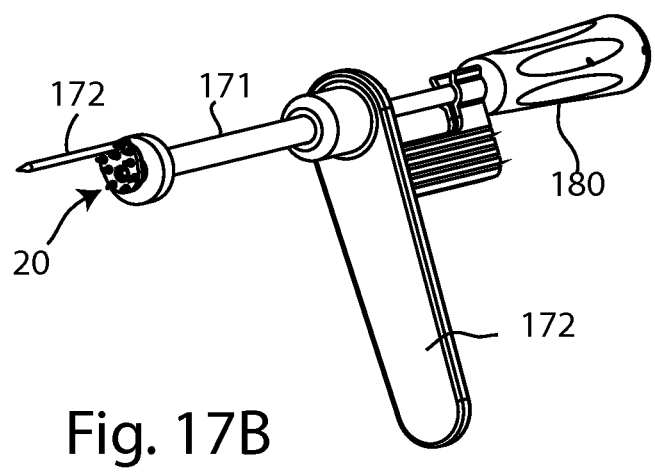
FIG. 17B shows an isometric view of the guide of FIG. 17A with a cap inserted into the guide.
Figure 17C:
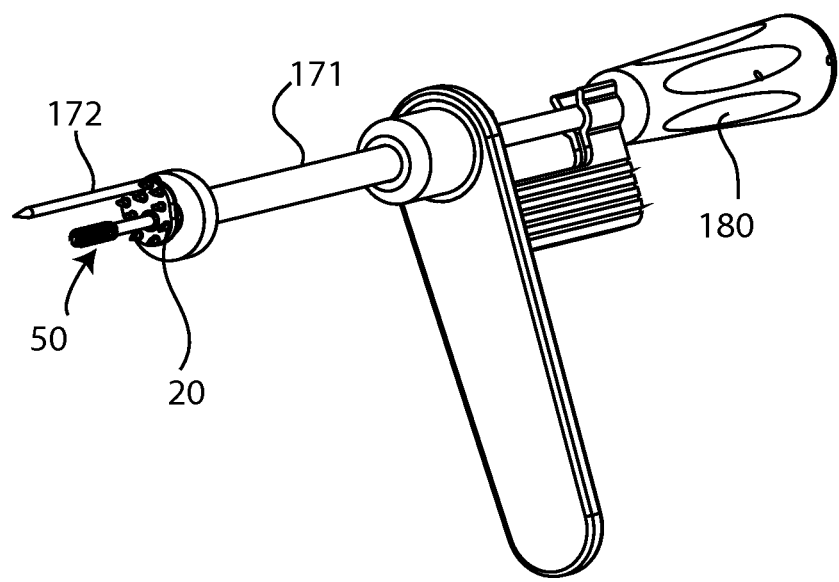
FIG. 17C shows an isometric view of the guide of FIG. 17A with a cap and fastener assembly inserted into the guide.
Figure 18:
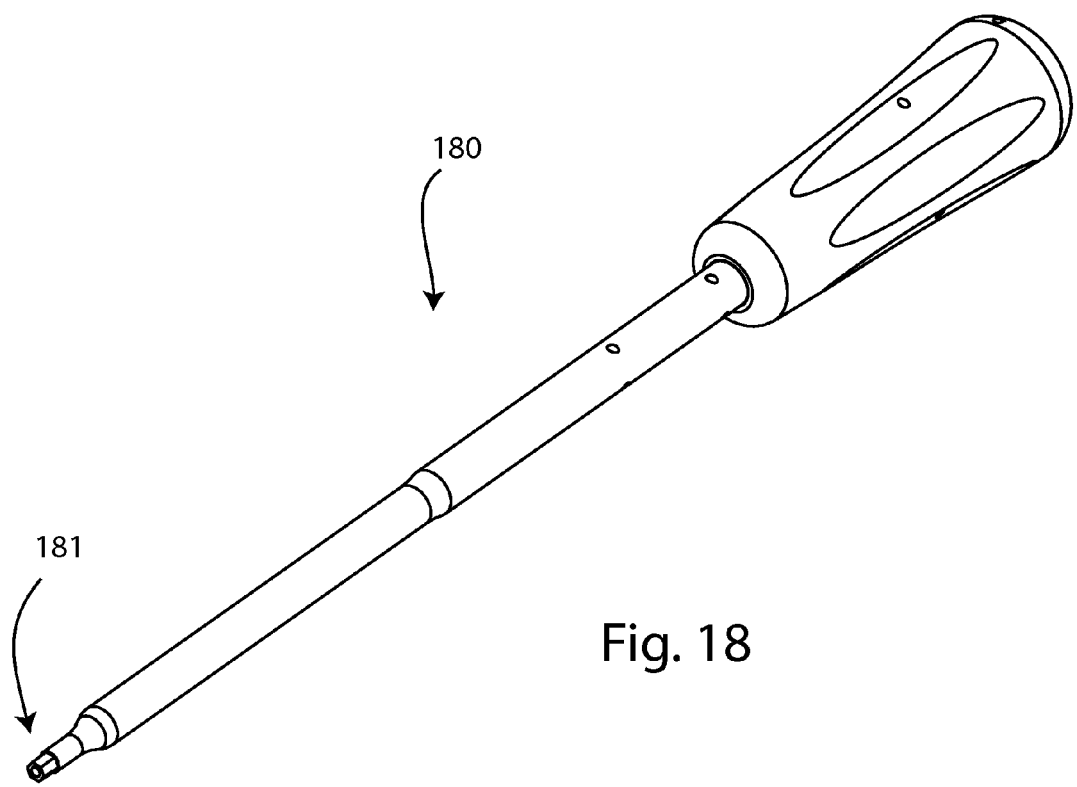
FIG. 18 shows an isometric view of a fastener driver in accordance with one example of the present disclosure.

FIG. 17A-17C show yet another example of a guide 170 for use with implants disclosed herein. The guide 170 can have a hollow shaft 171 and a guide pin 172. The guide pin 172 may be offset from a central longitudinal axis of the guide 170. The guide pin 172 cooperates with the slot 26 on the cap 20 to guide the cap 20 along a selected path into proper alignment with the joint. Guide pin 172 may also include a tip 173 which can act as a probe to aid in referencing the joint space. FIG. 17B shows the guide 170 with a cap 20 engaged with the guide 170 via a driver 180 and the guide pin 172. FIG. 17C shows the guide 170 engaged with a screw 50 and a cap 20 with the driver 180 pushing the cap 20 and screw 50 in the distal direction along the guide pin 172. FIG. 18 shows an isometric view of the driver 180 with a hexagonal tip 181. In other examples, the hexagonal tip 181 may be replaced with another shaped drive feature for connection with a suitable fastener.

All of the above guides can be used to orient, steer, and insert the implant to the desired location at the implant site where the driver 180 can then be used to apply a torsional rotation force to the fastener 50 to fasten the implant to the joint to stabilize the joint. Once the implant is in the proper location, the surgeon can remove the guide, the driver 180, the cannula 110, and the K-wire and then close the incision site.

It should be understood that the present components, systems, kits, apparatuses, and methods are not intended to be limited to the particular forms disclosed. Rather, they are intended to include all modifications, equivalents, and alternatives falling within the scope of the claims. They are further intended to include embodiments which may be formed by combining features from the disclosed embodiments, and variants thereof.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, a slot or tooth configuration from one or more examples may be combined with a cap from other examples. Similarly, manufacturing or assembly methods described for one cap may be used in the manufacture or assembly of another cap. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A bone fixation implant assembly, comprising:
   a fastener having a partially spherical fastener head having a head diameter and a shaft extending along a longitudinal axis; and
   an eccentrically shaped monolithic cap comprising:
   a first lobe;
   a second lobe adjoining the first lobe;
   a through aperture extending through the eccentrically shaped monolithic cap and configured to receive the fastener, the through aperture is offset from a geometric center of the cap, the through aperture comprising an aperture diameter and an aperture geometric center, the aperture exposed to a spherically shaped capsule comprising a lip having a lip diameter, wherein the aperture diameter is larger than the head diameter, the head diameter is larger than the lip diameter, and the fastener head is polyaxially retained within the spherically shaped capsule by the lip; and
   a pair of slots recessed into the cap on opposite sides of the aperture for interaction with a guide tool to hold the cap at a specific orientation; wherein:
   a first axis intersects an outer edge of the first lobe, an outer edge of the second lobe, and the aperture geometric center, the first axis defining an axis of maximum length of the cap, a second axis intersects the first axis at the aperture geometric center and extends perpendicular to the first axis, and the aperture defines an aperture axis perpendicular to the first and second axes;
   the first lobe of the eccentrically shaped cap is longer, when measured from the aperture geometric center to the outer edge of the first lobe along the first axis, than the second lobe of the eccentrically shaped cap, when measured from the aperture geometric center to the outer edge of the second lobe along the first axis;
   the first lobe of the eccentrically shaped cap comprises at least one width, wherein the at least one width is larger, when measured in the direction of the second axis perpendicular to the first axis, than a largest width of the second lobe, when measured in the direction of the second axis perpendicular to the first axis;
   the cap comprises a bone engaging side, each of the first and second lobes comprises a planar bone engaging surface on the bone engaging side and an upper surface opposite the planar bone engaging surface, wherein the planar bone engaging surface of the first lobe abuts and is coplanar with the planar bone engaging surface of the second lobe, providing a uniplanar surface on the bone engaging side of the cap, the uniplanar surface extending between the outer edges of the first and second lobes;

the spherically shaped capsule is contained entirely between the uniplanar bone engaging surface of the cap and the upper surface of the cap; and a plurality of teeth projecting from the first and second lobes on the bone engaging side continuous with the outer edges of the first and second lobes, said plurality of teeth configured to pierce into bone, the plurality of teeth comprising beveled surfaces which oppose one another and at least partially diverge away from each other moving away from the bone engaging side of the cap toward free ends of the teeth, and an additional tooth projecting from the planar bone engaging surface of the first lobe between one of the plurality of teeth and the aperture.

2. The assembly of claim 1, wherein the pair of slots extend into the cap intermediate the bone engaging side of the cap, and the upper surface, wherein the slot is shaped to receive a boss of the guide tool, in response to insertion of the boss into the slot along a direction non-parallel to the aperture to couple the cap to the guide tool, to facilitate positioning of the cap through the use of the guide tool.

3. The assembly of claim 1, wherein the upper surface of the first lobe of the eccentrically shaped cap tapers toward the planar bone engaging surface.

4. The assembly of claim 1, wherein the aperture is intermediate the first lobe and the second lobe.

5. The assembly of claim 1, wherein the additional tooth is located in an interior of the first lobe, and the plurality of teeth surround the additional tooth.

6. The assembly of claim 1, wherein the beveled surfaces of the plurality of teeth are flat.

7. The assembly of claim 1, wherein the fastener head is received within the capsule, and wherein the fastener is rotatable within the aperture and concentrically pivotable along its longitudinal axis.

8. The assembly of claim 3, wherein the upper surface tapers toward the planar bone engaging surface along the first lobe moving away from the second lobe toward the outer edge of the first lobe.

* * * * *